(12) United States Patent
Uenishi et al.

(10) Patent No.: US 8,589,121 B2
(45) Date of Patent: Nov. 19, 2013

(54) FRACTURE PREDICTION METHOD, PROCESSING DEVICE, PROGRAM PRODUCT AND RECORDING MEDIUM

(75) Inventors: Akihiro Uenishi, Tokyo (JP); Takashi Ariga, Tokyo (JP); Shigeru Yonemura, Tokyo (JP); Jun Nitta, Tokyo (JP); Tohru Yoshida, Tokyo (JP)

(73) Assignee: Nippon Steel & Sumitomo Metal Corporation, Tokyo (JP)

( * ) Notice: Subject to any disclaimer, the term of this patent is extended or adjusted under 35 U.S.C. 154(b) by 808 days.

(21) Appl. No.: 12/595,418

(22) PCT Filed: Apr. 14, 2008

(86) PCT No.: PCT/JP2008/057299
§ 371 (c)(1),
(2), (4) Date: Oct. 9, 2009

(87) PCT Pub. No.: WO2008/133092
PCT Pub. Date: Nov. 6, 2008

(65) Prior Publication Data
US 2010/0121621 A1 May 13, 2010

(30) Foreign Application Priority Data

Apr. 12, 2007 (JP) ................... 2007-105182

(51) Int. Cl.
*G06F 17/50* (2006.01)
*G06G 7/48* (2006.01)
*G01L 1/00* (2006.01)
*G01L 3/00* (2006.01)
*G01L 5/00* (2006.01)
*G06F 19/00* (2011.01)
*G06F 7/66* (2006.01)

(52) U.S. Cl.
USPC ............ 703/1; 703/7; 703/8; 702/41; 702/42; 702/43; 700/97; 700/98; 700/127

(58) Field of Classification Search
USPC ............ 703/1, 7, 8; 702/41–43; 700/98, 127, 700/223, 97
See application file for complete search history.

(56) References Cited

U.S. PATENT DOCUMENTS

2007/0199924 A1* 8/2007 Yoshida et al. ............... 219/109
2007/0282931 A1 12/2007 Suzuki et al.

FOREIGN PATENT DOCUMENTS

JP 8-339396 A 12/1996
JP 11-191098 A 7/1999
(Continued)

OTHER PUBLICATIONS

Lee, Young-Wong "Fracture Prediction in Metal Sheets", Feb. 2005, Department of Ocean Engineering, Massachusetts Institute of Technology, pp. 52, 53, 64-66, 135-146, 152-158, 161-163, 197-199, and 204-210.*

(Continued)

*Primary Examiner* — Kamini S Shah
*Assistant Examiner* — Cedric D Johnson
(74) *Attorney, Agent, or Firm* — Birch, Stewart, Kolasch & Birch, LLP

(57) ABSTRACT

When discretizing an analysis target part into plural elements and performing analysis, sheet thickness reduction rate or maximum principal strain at an equivalent position including a same element is compared by either a manner of combining two adjacent elements after the analysis or a manner of changing an element discretization size with two types and performing the analysis, and the element where the difference is large is extracted as a fracture risk portion. With this structure, a fracture risk portion can be extracted reliably when a fracture is predicted by a finite element method.

15 Claims, 10 Drawing Sheets

(56) References Cited

FOREIGN PATENT DOCUMENTS

| JP | 2000-107818 | A | 4/2000 |
|----|----|----|----|
| JP | 2002-60898 | A | 2/2002 |
| JP | 2005-017215 | | 1/2005 |
| JP | 2005-177837 | A | 7/2005 |
| JP | 2006-257506 | A | 9/2006 |
| TW | I263151 | B | 10/2006 |

OTHER PUBLICATIONS

Esche, Sven K. et al. "Numerical and Experimental Investigation of Redrawing of Sheet Metals", 2000, Journal of Materials Processing Technology 98, Elsevier Science S.A.*

Brokken D. et al. "Predicting the Shape of Blanked Products: A Finite Element Approach", 2000, Journal of Materials Pressing Technology 103, Elsevier Science S.A.*

Leu, Daw-Kwei, "Finite-Element Simulation of Hole Flanging Process of Circular Sheets of Anisotropic Materials", 1996, International Journal of Mechanical Sciences, vol. 38, Nos. 8-9, Elsevier Science Ltd.*

Cherouat, A. et al., "Numerical Improvement of Thin Tubes Hydroforming with Respect to Ductile Damage", 2003, International Journal of Mechanical Sciences 44, Elsevier Science Ltd.*

Written Opinion dated Jul. 15, 2008.

Office Action in Taiwanese Application No. 97113554 mailed Sep. 21, 2011, including an English summary.

L. Wang et al., "The effect of yield criteria on the forming limit curve prediction and the deep drawing process simulation", International Journal of Machine Tool & Manufacture, vol. 46, No. 9, Jul. 1, 2006, pp. 988-995.

Z. Q. Sheng et al., "FEM analysis and design bulb shield progressive draw die", Journal of Materials Processing Technology, vol. 189, No. 1-3, Apr. 7, 2007, pp. 58-64.

Z. Q. Sheng et al., "FEM-based progressive drawing process design", The International Journal of Advanced Manufacturing Technology, (2008), vol. 36, No. 3-4, pp. 226-236.

European Search Report in corresponding European Application No. 08740385.3 dated May 27, 2011.

Russian Office Action in Corresponding Russian Application No. 2009141717, dated Dec. 15, 2010 with English Translation.

* cited by examiner

FIG. 2

| n | CONTROL PARAMETER(L*) 1/n | COARSE AREA DISCRETIZATION UPPER LIMIT(mm) 10 | COARSE AREA DISCRETIZATION LOWER LIMIT(mm) 2 | FINE AREA DISCRETIZATION UPPER LIMIT(mm) 5 | FINE AREA DISCRETIZATION LOWER LIMIT(mm) 0.5 |
|---|---|---|---|---|---|
| 1 | 1 | 9.995475829 | 1.999095166 | 4.997737915 | 0.499773791 |
| 2 | 0.5 | 9.993450202 | 1.99869004 | 4.996725101 | 0.49967251 |
| 3 | 0.333333 | 9.99051763 | 1.998103526 | 4.995258815 | 0.495525882 |
| 4 | 0.25 | 9.986272045 | 1.997254409 | 4.993136022 | 0.499313602 |
| 5 | 0.2 | 9.980125564 | 1.996025113 | 4.990062782 | 0.499006278 |
| 6 | 0.166667 | 9.971227091 | 1.994245418 | 4.985613546 | 0.498561355 |
| 7 | 0.142857 | 9.958344464 | 1.991668893 | 4.979172232 | 0.497917223 |
| 8 | 0.125 | 9.939693838 | 1.987938768 | 4.969846919 | 0.496984692 |
| 9 | 0.111111 | 9.912692682 | 1.982538536 | 4.956346341 | 0.495634634 |
| 10 | 0.1 | 9.873602174 | 1.974720435 | 4.936801087 | 0.493680109 |
| 11 | 0.090909 | 9.817009492 | 1.963401898 | 4.908504746 | 0.490850475 |
| 12 | 0.083333 | 9.735078307 | 1.947015661 | 4.867539154 | 0.486753915 |
| 13 | 0.076923 | 9.616463695 | 1.923292739 | 4.808231848 | 0.480823185 |
| 14 | 0.07149 | 9.444741216 | 1.888948243 | 4.722370608 | 0.472237061 |
| 15 | 0.066667 | 9.191132638 | 1.839226528 | 4.598066319 | 0.459806632 |
| 16 | 0.0625 | 8.836213394 | 1.767242679 | 4.418106697 | 0.44181067 |
| 17 | 0.058824 | 8.315145847 | 1.663029169 | 4.157572923 | 0.415757292 |
| 18 | 0.055556 | 7.560778321 | 1.512155664 | 3.780389161 | 0.378038916 |
| 19 | 0.052632 | 6.468654343 | 1.293730869 | 3.234327172 | 0.323432717 |
| 20 | 0.05 | 4.887548656 | 0.977509731 | 2.443774328 | 0.244377433 | he present invention is made in view of the above-described problems, and an object thereof is to provide a fracture prediction method for extracting a fracture risk portion easily and reliably when predicting a fracture by the finite element method, a processing device, a program product and a recording medium.

FRACTURE PREDICTION METHOD, PROCESSING DEVICE, PROGRAM PRODUCT AND RECORDING MEDIUM

TECHNICAL FIELD

The present invention relates to a fracture prediction method for extracting a fracture risk portion when performing deformation analysis by a finite element method, a processing device, a program product and a recording medium.

BACKGROUND ART

In recent years, in the automobile industry, it has become an urgent problem to develop a vehicle structure capable of reducing injuries to a passenger at a time of collision. On the other hand, reduction in weight of the vehicle body is also important for improving fuel efficiency. For solving these problems, application of materials with higher strength, high-strength steel sheets as steel materials in particular, is considered. However, generally it is said that increase in strength leads to deterioration in formability. For expanding application, it is important to improve formability, particularly, stretch flange formability.

For solving such problems, development of a material with excellent stretch flange formability is in progress. For example, in Patent Document 1, there is disclosed a material with stretch flange formability improved by controlling microstructure such as ferrite and bainite. Further, in Patent Document 2, there are disclosed aluminum alloy sheets with excellent stretch flange formability by defining plastic anisotropy and uniform elongation in a tensile test in a specific direction.

However, formability in an actual part is determined not only by material properties, but is affected by die configuration, lubricating conditions, forming conditions, and/or the like in a complicated manner. Therefore, it is necessary to set these complicated factors appropriately, together with materials, so as to take advantage of excellent material properties. For such purposes, numerical analysis techniques are applied.

In Patent Document 3, there is disclosed a method of predicting a fracture or a wrinkle, which is a forming defect at the time of formation, using a finite element method. According to this method, analysis is performed with the finite element method, and generation of fracture or wrinkle is determined using data of strain and/or stress of an element of interest. However, when using such a method, it is required to perform element discretization by an appropriate size according to the analysis target. When analysis is performed with inappropriate element discretization, there is a fear that the prediction results in over or under estimation and hence does not correspond to the reality.

[Patent Document 1] Japanese Patent Application Laid-open No. 2002-60898
[Patent Document 2] Japanese Patent Application Laid-open No. 2006-257506
[Patent Document 3] Japanese Patent Application Laid-open No. Hei 8-339396

SUMMARY OF THE INVENTION

As described above, it has been very difficult to extract a fracture risk portion reliably by the conventional arts when predicting generation of a fracture or a wrinkle, which is a forming defect at the time of forming, using the finite element method.

The present invention is made in view of the above-described problems, and an object thereof is to provide a fracture prediction method for extracting a fracture risk portion easily and reliably when predicting a fracture by the finite element method, a processing device, a program product and a recording medium.

The present inventors considered the fracture prediction method while focusing attention on that deformation localizes on a fracture risk portion and a large deformation gradient occurs around the portion, and found that the fracture risk portion can be determined reliably. The gist of the present invention is as follows.

1. A fracture prediction method includes:
a first step of discretizing an analysis target part by a first area and a second area larger than the first area respectively and performing forming analysis using a finite element method;
a second step of calculating maximum principal strain or sheet thickness reduction rate for each of the part discretized by the first area and the second area; and
a third step of extracting a fracture risk portion from the analysis target part discretized by the first area, where difference of maximum principal strain or sheet thickness reduction rate between calculated values in the part discretized by the first area and those in the part discretized by the second area is larger than a predetermined value at a position corresponding to a same portion on the analysis target part.

2. In the fracture prediction method according to 1., in the first step, a size of the first area and a size of the second area are determined by a relationship with n value of the analysis target part.

3. In the fracture prediction method according to 1. or 2., in the third step, when a fracture risk portion where the difference is larger than the predetermined value is not extracted, at least the first area out of the first area and the second area is set smaller, and the first step, the second step and the third step are executed again sequentially.

4. In the fracture prediction method according to any one of 1. to 3., in the first step, an edge portion of the analysis target part is discretized by the first area and the second area respectively, and then the forming analysis is performed.

5. A fracture prediction method includes:
a first step of discretizing an analysis target part into plural areas and performing forming analysis using a finite element method;
a second step of calculating maximum principal strain or sheet thickness reduction rate for each of the areas;
a third step of combining adjacent two or more of the areas and calculating maximum principal strain or sheet thickness reduction rate in the combined area; and
a fourth step of extracting, as a fracture risk portion of the analysis target part, the area where difference of the maximum principal strain or the sheet thickness reduction rate before and after combining the areas is larger than a predetermined value.

6. In the fracture prediction method according to 5., in the first step, an edge portion of the analysis target part is discretized by the area and then the forming analysis is performed.

7. A processing device used for fracture prediction method of an analysis target part includes:
a first unit discretizing an analysis target part by a first area and a second area larger than the first area respectively and performing forming analysis using a finite element method;
a second unit calculating maximum principal strain or a sheet thickness reduction rate for each of the part discretized by the first area and the second area; and a third unit extracting a fracture risk portion from the analysis target part discretized by the first area, where difference of maximum principal strain or sheet thickness reduction rate between calculated values in the part discretized by the first area and those in the part discretized by the second area is larger than a predetermined value at a position corresponding to a same portion on the analysis target part.

8. In the processing device according to 7., the first unit determines a size of the first area and a size of the second area by a relationship with n value of the analysis target part.

9. A processing device used for fracture prediction method of an analysis target part includes:

a first unit discretizing an analysis target part into plural areas and performing forming analysis using a finite element method;

a second unit calculating maximum principal strain or a sheet thickness reduction rate for each of the areas;

a third unit combining adjacent two or more of the areas and calculating the maximum principal strain or sheet thickness reduction rate in the combined area; and a fourth unit extracting, as a fracture risk portion of the analysis target part, the area where difference of the maximum principal strain or the sheet thickness reduction rate before and after combining the areas is larger than a predetermined value.

10. A program product causes a computer to execute:

a first step of discretizing an analysis target part by a first area and a second area larger than the first area respectively and performing forming analysis using a finite element method;

a second step of calculating maximum principal strain or sheet thickness reduction rate for each of the part discretized by the first area and the second area; and a third step of extracting a fracture risk portion from the analysis target part discretized by the first area, where difference of maximum principal strain or sheet thickness reduction rate between calculated values in the part discretized by the first area and those in the part discretized by the second area is larger than a predetermined value at a position corresponding to a same portion on the analysis target part.

11. In the program product according to 10., in the first step, a size of the first area and a size of the second area are determined by a relationship with n value of the analysis target part.

12. In the program product according to 10. or 11., in the third step, when a fracture risk portion where the difference is larger than the predetermined value is not extracted, at least the first area out of the first area and the second area is set smaller, and the first step, the second step and the third step are executed again sequentially.

13. In the program product according to any one of 10. to 12., in the first step, an edge portion of the analysis target part is discretized by the first area and the second area respectively, and then the forming analysis is performed.

14. A program product causes a computer to execute:

a first step of discretizing an analysis target part into plural areas and performing forming analysis using a finite element method;

a second step of calculating maximum principal strain or sheet thickness reduction rate for each of the areas;

a third step of combining adjacent two or more of the areas and calculating maximum principal strain or sheet thickness reduction rate in the combined area; and a fourth step of extracting, as a fracture risk portion of the analysis target part, the area where difference of the maximum principal strain or the sheet thickness reduction rate before and after combining the areas is larger than a predetermined value.

15. In the program product according to 14., in the first step, an edge portion of the analysis target part is discretized by the area and then the forming analysis is performed.

16. A computer readable recording medium recording a program product according to any one of 10. to 15.

By performing fracture prediction of a part to be processed based on the present invention, dependency on selection of analysis conditions can be reduced, and a fracture risk portion can be extracted easily and reliably. Accordingly, the costs needed for development can be reduced, and weight reduction is realized by applying a material having higher strength to a part to be processed.

BRIEF DESCRIPTION OF THE DRAWINGS

FIG. 2 is a table showing simulation results when determining upper and lower limits of coarse and fine element discretization;

DETAILED DESCRIPTION OF THE PREFERRED EMBODIMENTS

Figure 1:
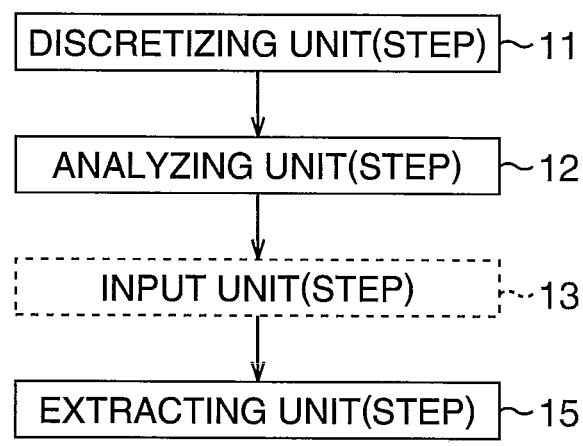
FIG. 1 is a flowchart of a fracture prediction method (device) of the present invention.

First, the present inventors examined deformation states of fracture portions of analysis target parts in detail. Consequently, it was found that, there is a peak at a position where a fracture actually occurs and deformation such as a sheet thickness reduction rate or strain decreases by degrees in the vicinity of this peak. Specifically, it is conceivable that after deformation concentrates in some area (element) in an analysis target part, localization of the deformation occurs further in the area, and it eventually leads to a fracture. This means that, in other words, in a fracture portion of an analysis target part, a so-called deformation gradient is large. The deformation gradient is variation (gradient) depending on a position of a deformation amount such as sheet thickness reduction rate or strain amount in a certain portion of an analysis target part. The deformation gradient is a differential coefficient obtained by differentiating a deformation amount by a position (distance), and can be represented for example by, considering a minute area, deformation gradient=[deformation amount/distance (mm)].

As a conventional method for distinguishing a fracture by performing deformation analysis of an analysis target part by a finite element method, generally there is adopted a method to compare a deformation amount of each area (each element discretized in a mesh form) obtained by calculation with a fracture limit of a material that is obtained separately. Specifically, in the conventional method, during the deformation analysis using the finite element method, a portion is determined as a fracture risk portion when a deformation amount in a certain element exceeds a fracture limit defined based on the fracture limit of a material of the analysis target part.

However, in this case, problems occur as follows.

In the finite element method, the deformation amount calculated for each element will be the average value within this element. Therefore, when the element size is set to be relatively large, in an element in which a portion with a large deformation amount exists, this portion exists locally in a narrow area in the element of interest. In this case, even when the fracture limit is exceeded locally in the portion of interest, averaging of deformation amounts in the element results in that, so to speak, the deformation amount of the portion of interest is embedded in the average value, and thus the output value as the average in the element does not exceed the fracture limit. In this case, the portion of interest cannot be determined as the fracture risk portion.

Accordingly, to deal with the localization of deformation, discretization into adequately small elements is conceivable.

However, in the finite element method, the calculation time depends largely on the element size and the total number of elements. When discretizing into adequately small elements which can deal with the localization of deformation, a quite long time is required for deformation analysis. Specifically, the processing time is proportional to the inverse number of the cube of a reduction rate of the element size. For example, the calculation time becomes about eight times longer when the element size is reduced to ½, and about 64 times longer when the element size is reduced to ¼. While use of an element with one side being 2 mm requires approximately ten hours of calculation time for the scale of a normal analysis target part for example, use of an element with one side being 0.5 mm so as to improve the accuracy requires approximately 64 times longer, 640 hours, of calculation time, which lacks practicality.

Further, when the element size is small, a problem as follows also occurs. Specifically, when using an element size smaller than the gauge length (gauge length to be the reference when a strain of a fracture portion is measured) at the time of obtaining the fracture limit of a material of the analysis target part, an output value from the element and the fracture limit cannot be compared directly. In this case, some kind of correction is required.

Moreover, in the first place, no matter how small the discretized element size, there may be a case where the possibility of fracture generation cannot be determined accurately. Specifically, even when a portion having a deformation amount as large as is sufficient for generation of fracture exists in the analysis target part, there may be a case where the portion of interest has a substantially uniform deformation amount over a relatively large area, and a fracture does not occur because there is no localization of deformation therein. An example is so-called burring deformation such that a substantially uniform deformation amount occurs in the periphery of a hole formed in the analysis target part. In such a case, although no fracture occurs actually, an output value in the element corresponding to the portion of interest exceeds the fracture limit, and the portion may be determined as a fracture risk portion.

As explained above, in the conventional fracture determination method, it is required to have a high degree of expertise for performing precise fracture determination, and also it is possible to miss a fracture risk portion depending on the form of occurrence of deformation and/or setting conditions.

To improve this situation, the present inventors focused attention on that a deformation gradient is large around a fracture risk portion, and thereby devised a new fracture determination method that uses the point that averaging depending on the element size is performed in analysis by the finite element method.

According to the present invention, two types of elements (here, for convenience, the smaller one is referred to as first element, and the larger one as second element) having different sizes of discretization in the finite element method is used for conducting analysis for a portion having a deformation gradient. In the finite element method, a deformation amount in an element of interest is averaged and outputted. Therefore, in the case where a deformation portion having a large deformation gradient exists in a certain element, for when the element of interest is the first element and when it is the second element, the former becomes the larger output value than the latter.

According to the present invention, difference between calculated average values in the part discretized by the first element and those in the part discretized by the second element is used to extract a fracture risk portion for the first element and the second element separately at a position corresponding to the same portion in the analysis target part. In this case, when outputs of average values are different between the first element and the second element, it is conceivable that a deformation gradient exists in the element of interest. This difference between output values corresponds to the degree of the deformation gradient. The larger the deformation gradient, the higher the risk of fracture, and the degree of fracture risk can be determined by the difference between analysis values.

According to the present invention, a possible structure is such that, after analyzing with elements having a predetermined size instead of using two types of elements having different discretization sizes as described above, two or more elements are combined so as to take the difference between output values before and after combining the elements. In this case, when outputs of average values before and after combining the elements are different, it is conceivable that a deformation gradient exists in the elements of interest. The larger the deformation gradient, the higher the risk of fracture, and the degree of fracture risk can be determined by the difference between analysis values.

As the analysis values mentioned here, any value can be used such as sheet thickness, sheet thickness reduction rate, maximum principal strain, forming allowance in a forming limit diagram represented by maximum and minimum principal strains, or the like, used generally in fracture determination. It is desirable to use the sheet thickness reduction rate or the maximum principal strain due to easiness of handling in analysis. Further, in finite element method analysis of forming process, generally as an element, a shell (two-dimensional) element constituted of several nodes in a plane but has no node in the thickness direction is used, and the present invention is preferable for this element. However, the present invention can be applied in exactly the same manner to a one-dimensional element (bar element) used for processed products in a bar shape, and a three-dimensional element (solid element) used for improving analytical accuracy of a deformation in the thickness direction in more detail.

It was found that, using such a method, it is possible to perform simply and reliably fracture determination that has been difficult conventionally unless the element size is optimized because of dependence on the degree of local deformation of a fracture risk portion, a measurement method when determining a fracture limit, or the like.

Specifically, according to the present invention, all the above-described problems in the conventional art can be solved.

Specifically, according to the present invention, as the first element or the element before combining, it is not necessary to use an element having a very small size as in the conventional art, and therefore a significant reduction of processing time is realized. Also in this case, it is not necessary to use an element size smaller than the gauge length at the time of obtaining the fracture limit of a material of the analysis target part, and hence it becomes possible to compare the output value from an element and the fracture limit directly.

According to the present invention, by making use of a point in a reverse sense, so to speak, that the deformation amount is averaged in an element by the finite element method, two types of elements having different sizes are used. Therefore, whereas conventionally contribution of a portion having a large deformation amount is, so to speak, embedded in the average value by averaging of a deformation amount in an element, the present invention allows to determine a fracture risk portion precisely.

Further, as in the burring deformation, even when a portion having a deformation amount as large as is sufficient for generation of fracture exists in the analysis target part, the present invention can handle even the case where the portion of interest has a substantially uniform deformation amount over a relatively large area, and a fracture does not occur because there is no localization of deformation therein. Specifically, in this case, the portion of interest has a small deformation gradient (or substantially no deformation gradient), and hence taking a difference between output values of the first element and the second element results in a relatively small value, which can be determined precisely as not being a fracture risk portion.

Further, as a result of dedicated studies conducted by the present inventors, it was found that the accuracy of fracture determination increases significantly as compared to the conventional method for, among various kinds of fractures, the form of deformation which is called a stretch flange fracture. Stretch flange forming can be seen at a root portion of a center pillar that is a portion of a body side panel, a flange-up processed portion for welding of members, or the like, and a deformation state thereof is close to a uniaxial tension. In such a deformation mode, the deformation gradient of a fracture risk portion is quite large. Further, the deformation is more local compared to other fracture forms. Therefore, generally it is necessary to use a quite small element when performing analysis by the finite element method. This makes the calculation time excessive, and it is difficult to couple the calculated value to the fracture limit value of a material measured by a certain specific gauge length.

In contrast, with the present invention, it was found that the deformation gradient can be evaluated as a difference of analysis values by changing sizes of elements for calculating the analysis values, and a fracture risk portion can be extracted reliably. When the present invention is applied to high-strength steel sheets having ultimate tensile strength of 440 MPa or higher, in which the stretch flange fracture might occur easily in relation with the deformation gradient, prediction accuracy thereof improves significantly, and thus the present invention is preferable for such application.

In addition, the present invention is not limited to the finite element method, and can be applied to any analysis method as long as it performs element discretization. Further, the invention is effective for prediction of not only a fracture during formation but a fracture of a material at the time of deformation by collision.

Hereinafter, the present invention will be explained specifically.

The present invention according to 1., as shown in FIG. 1, when an analysis target part is discretized into plural areas (elements) and formation analysis is performed by the finite element method, two types of elements, an element having a small size (first element) and an element (second element) larger than the first element, are used to perform the formation analysis (discretizing unit (step) 11), and the sheet thickness reduction rate or the maximum principal strain is calculated for each of the elements (analyzing unit (step) 12). Thereafter, the first element where a difference value of the maximum principal strain or the sheet thickness reduction rate between the first element and the second element is larger than a predetermined value at a position corresponding to the same portion on the analysis target part is extracted as a fracture risk portion of the analysis target part (extracting unit (step) 15).

Here, the discretizing unit 11, the analyzing unit 12 and the extracting unit 15 are realized as functions of a central processing unit (CPU) of a computer for example.

Figure 5:
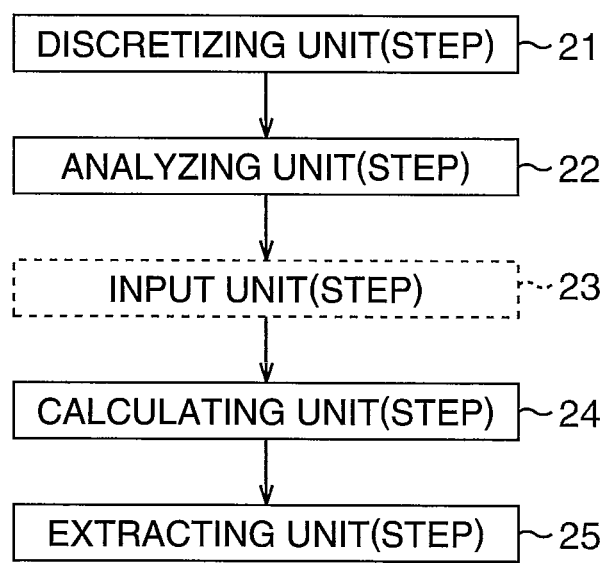
FIG. 5 is a flowchart of a fracture prediction method (device) of the present invention.

Note that in FIG. 1 and FIG. 5, a solid line denotes a required unit or step, and a dashed line denotes an alternative unit or step.

First, to discretize the analysis target part into plural elements (discretizing unit (step) 11), the analysis target part is expressed by digital data (CAD data or shape measurement data) of a three-dimensional shape of the part as an aggregate of two-dimensional planer areas. At this time, a corner portion of the part is discretized by sufficiently small elements because it changes in shape largely, to thereby ensure shape reproducibility. Further, when analyzing a stretch flange fracture in an edge portion, it is preferable that element discretization is performed so that the outer peripheral line of the part is smooth without any projection or recess. Further, when performing the element discretization by the first element and the second element with different sizes, the entire analysis target part may be uniformly discretized finely (or coarsely), or some areas of the part where the fracture determination is performed may be discretized finely or coarsely. The former is convenient in terms of operation steps, and the latter is advantageous for reducing the calculation time. Therefore, the both may be selected or combined appropriately considering the overall load.

Here, in the discretizing unit (step) 11, a size of the first element and a size of the second element are determined by a relationship with n value of the analysis target part.

According to the present invention, when performing analysis with the element discretization by the finite element method, the element discretization should be performed sufficiently finely so as to reproduce the geometrical shape of a target portion, namely, the curvature of an edge portion, the radius of curvature of a corner portion, or the like for example. Further, according to the present invention, when analysis is performed with the element discretization being changed with two types, the first element and the second element, and thereafter a difference of the sheet thickness reduction rate or the maximum principal strain is taken between the first element and the second element, extra care should be taken for the two element discretization sizes (coarse and fine). The present inventors conducted dedicated studies on a setting method of the coarse and fine element discretization sizes, and found that the sizes are related to the work hardening property of a material. It was found that excellent fracture prediction accuracy can be obtained when an average size "L coarse" (in units of mm) of the coarse element discretization and an average size "L fine" (in units of mm) of the fine element discretization satisfy the following relationship, with the work hardening property of a material being represented by n value that is obtained generally by a tensile test:

$$f(2,n) \leq L\ \text{coarse} \leq f(10,n) \quad (1)$$

$$f(0.5,n) \leq L\ \text{fine} \leq f(5,n) \quad (2)$$

Here, n is n value of the material, and the above expressions are satisfied when n≥0.05. When n<0.05, a value of n=0.05 may be used to obtain the L coarse and the L fine. Further, a function f(L*, n) is given as follows:

$$f(L^*,n) = L^*(1-\exp(0.37/n)/3200) \quad (3)$$

In other words, the above expressions (1) to (3) become:

$$2(1-\exp(0.37/n)/3200) \leq L\ \text{coarse} \leq 10(1-\exp(0.37/n)/3200) \quad (4)$$

$$0.5(1-\exp(0.37/n)/3200) \leq L\ \text{fine} \leq 5(1-\exp(0.37/n)/3200) \quad (5)$$

This function f has a value that gets larger together with n value. Localization of deformation does not occur easily when the n value is large, and hence the fracture prediction accuracy can be assured even by element discretization with a large size. On the other hand, deformation can easily occur locally when the n value is small. Thus, the deformation gradient of a fracture risk portion becomes large, and the fracture prediction accuracy lowers unless element discretization by a sufficiently small size is performed. Accordingly, the element discretization size needs to be made small, and hence such setting is made.

Figure 3:
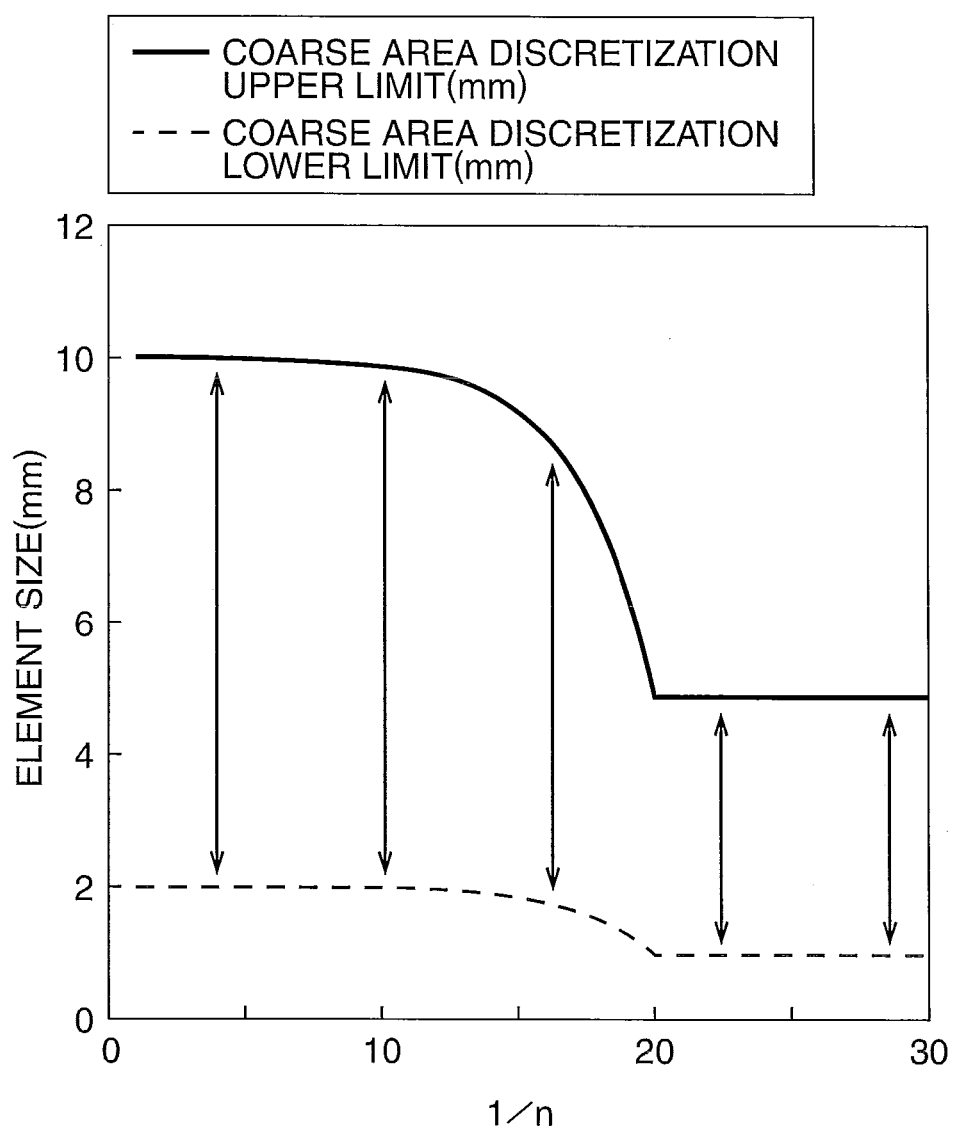
FIG. 3 is a characteristic chart showing simulation results when determining the upper and lower limits of the coarse element discretization.
Figure 4:
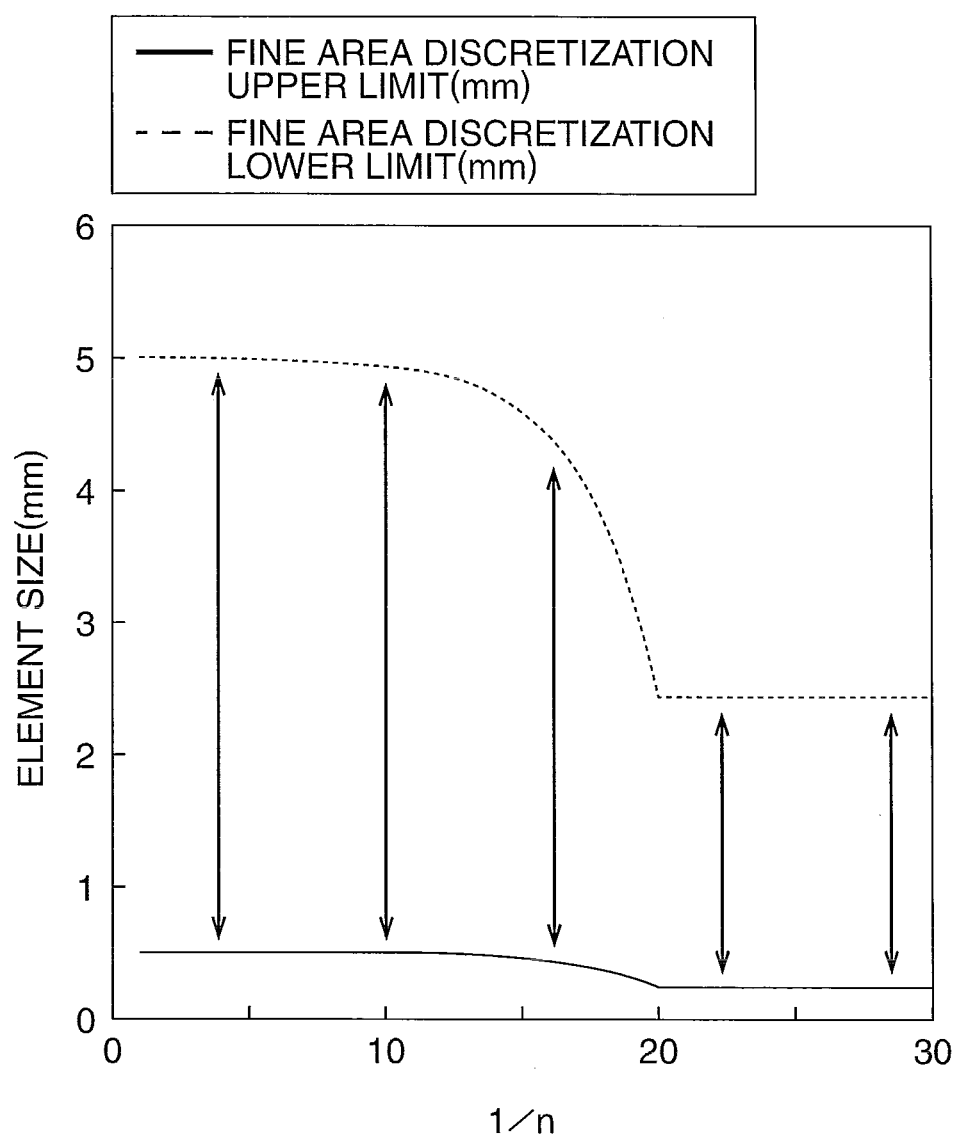
FIG. 4 is a characteristic chart showing simulation results when determining the upper and lower limits of the fine element discretization.

Although it was anticipated that it is better to perform the element discretization by a small size when the n value is quite small, smaller than 0.05, the element discretization by a too small size can lead to increase of calculation time and hence not preferable. Thus, it was found that, even when the coarse/fine element discretization set with the n value being 0.05 is used, there is no problem in practice in the range of accuracy of numeric analysis by the current finite element method. Accordingly, when the n value is 0.05 or smaller, the element discretization may be set with the n value being 0.05. Results of simulation when determining upper and lower limits of the coarse and the fine element discretization are shown in FIG. 2, and characteristic charts are shown in FIG. 3 and FIG. 4.

When evaluating the deformation gradient with higher accuracy, the ratio between the L coarse and the L fine, L coarse/L fine may be 1.5 or larger, preferably 2 or larger.

Next, when performing formation analysis by the finite element method, as commercially available software, incremental type software such as PAM-STAMP, LS-DYNA, one-step type software such as AutoForm, HyperForm, or the like for example is used for conducting forming analysis of an entire part, and the sheet thickness reduction rate or the maximum principal strain of each of the first elements and each of the second elements are calculated (analyzing unit (step) 12). The sheet thickness reduction rate and the maximum principal strain are calculated as values of the final shape for performing fracture determination from histories of plastic strain increments used by the finite element method. As formation analysis, the present invention can be used for forming accompanying hole expansion processing, flange-up forming, any press forming such as stretching or deep-drawing, hydro-pressure forming jointly using an internal pressure, hydro-forming operating axial force and internal pressure on a pipe, and the like.

Here, a difference of the above-described sheet thickness reduction rate or maximum principal strain is calculated as a difference between extracted elements of other analysis results, which are closest to the position of the element of interest on the basis of analysis results from the element discretization by the smallest size.

Then an element with a difference of the above-described sheet thickness reduction rate or maximum principal strain being larger than a predetermined value is extracted as a fracture risk portion (extracting unit (step) 15).

Here, the aforementioned predetermined value can be obtained as a fracture limit value by a separately performed experiment, or obtained as a value corresponding to the size of a combined element after performing formation analysis of a simple shape part.

Specifically, for example, when an element with one side being 2 mm is used as the first element, and an element with one side being 4 mm is used as the second element, the predetermined value when the deformation amount is the maximum principal strain is preferred to be within the range of 0.01 to 0.50. Here, with a value smaller than 0.01, it is possible that misjudgment occurs due to the influence of errors of numerical analysis, or there is a fear that even a portion having a relatively small deformation gradient is recognized as a fracture risk portion. With a value larger than 0.50, there is a fear that even a portion having a relatively large deformation gradient cannot be recognized as a fracture risk portion. Thus, it is not possible to identify a deformation portion with high accuracy. Therefore, a value within the range of 0.01 to 0.50 is preferable.

Preferably, in the aforementioned range, a value within the range of 0.03 to 0.20 is preferable. More preferably, a value within the range of 0.05 to 0.10 is preferable.

On the other hand, the predetermined value when the deformation amount is the sheet thickness reduction rate is preferred to be within the range of 0.01 to 0.25. Here, with a value smaller than 0.01, it is possible that misjudgment occurs due to the influence of errors of numerical analysis, or there is a fear that even a portion having a relatively small deformation gradient is recognized as a fracture risk portion. With a value larger than 0.25, there is a fear that even a portion having a relatively large deformation gradient cannot be recognized as a fracture risk portion. Thus, it is not possible to identify a deformation portion with high accuracy. Therefore, a value within the range of 0.01 to 0.25 is preferable.

Preferably, in the above range, a value within the range of 0.02 to 0.15 is preferable. More preferably, a value within the range of 0.025 to 0.10 is preferable.

The above-described analysis (analyzing unit (step) 12) and extraction (extracting unit (step) 15) may be executed in the same computer. Alternatively, after the analysis (analyzing unit (step) 12) is executed in one computer, the sheet thickness reduction rate or the maximum principal strain of each of two or more elements from the element discretization being changed in size as analysis results thereof may be inputted to another computer (input unit (step) 13) so as to execute the extraction (extracting unit (step) 15).

In the present invention according to 2., as described above using FIG. 2 to FIG. 4, in the discretizing unit (step) 11 a size of the first element and a size of the second element are determined by a relationship with n value of the analysis target part.

In the present invention according to 3., in the extraction (extracting unit (step) 15) of fracture risk portion, when the first element where the difference value is larger than the predetermined value is not extracted, at least the first element out of the first element and the second element is set smaller, and then the discretization (discretizing unit (step) 11), the calculation (analyzing unit (step) 12) of the sheet thickness reduction rate or the maximum principal strain of each element, and extraction (extracting unit (step) 15) of a fracture risk portion are executed again sequentially.

In the present invention according to 4., in the discretizing unit (step) 11 of FIG. 1, an edge portion of the analysis target part is discretized into plural elements and then forming analysis is performed, and in the extracting unit (step) 15, one of the edge portions is extracted as a fracture risk portion.

To divide the edge portion of the analysis target part into plural elements, the discretization is performed so that the element discretization size surely changes particularly in the portion where the fracture determination is performed. In the edge portion where the fracture determination is performed, elements should be connected smoothly without any recess and/or projection in either case of large and small element discretization sizes. Further, for reliably performing the fracture determination in the edge portion, it is important to evaluate a deformation gradient along the edge portion, and it is desirable that the element discretization size surely changes in the direction along the edge portion (refer to FIG. 8A and FIG. 8B).

When extracting one of the edge portions as a fracture risk portion, similarly to the invention according to 1., a portion of an element where a difference of the sheet thickness reduction rate or the maximum principal strain of each predetermined element is larger than the predetermined value is extracted as a fracture risk portion.

In the present invention according to 5., as shown in FIG. 5, an analysis target part is discretized into plural elements (discretizing unit (step) 21), forming analysis is performed by the finite element method, and the sheet thickness reduction rate or the maximum principal strain is calculated for each element (analyzing unit (step) 22). Thereafter, adjacent two or more of the elements are combined, the sheet thickness reduction rate or the maximum principal strain in the combined element is calculated (calculating unit (step) 24), and the element where a difference of the sheet thickness reduction rate or the maximum principal strain before and after combining is larger than a predetermined value is extracted as a fracture risk portion (extracting unit (step) 25).

Here, the discretizing unit 21, the analyzing unit 22, the calculating unit 24 and the extracting unit 25 are realized as functions of a central processing system (CPU) of a computer for example.

First, to discretize the analysis target part into plural elements (discretizing unit (step) 21), the analysis target part is expressed by digital data (CAD data or shape measurement data) of a three-dimensional shape of the part as an aggregate of two-dimensional planar regions. At this time, a corner portion of the part is discretized by sufficiently small elements because it changes in shape largely, to thereby ensure shape reproducibility. Further, when analyzing a stretch flange fracture in an edge portion, it is preferable that element discretization is performed so that the outer peripheral line of the part is smooth without any projection or recess.

Next, the same type of software as for the analysis of FIG. 1 (analyzing unit (step) 12) is used to perform the same formation analysis as in the invention of 1., and forming analysis of the entire part is performed, so as to calculate the sheet thickness reduction rate or the maximum principal strain of each element of interest (analyzing unit (step) 22). The calculation of the sheet thickness reduction rate and the maximum principal strain is the same as in the analysis of FIG. 1 (analyzing unit) step 12).

Next, to combine two or more adjacent elements, a calculated value in each element as a target of combining and information of the position (coordinates) of each element are needed. The calculated value of the element after combining (sheet thickness reduction rate or maximum principal strain) is the arithmetic average of calculated values of the respective elements. The position of the element after combining is the arithmetic average of the positions of the respective elements, or more simply, the position of the central element may be inherited as it is.

Then, with elements at closest positions from each other when compared before and after the combining being extracted respectively, a difference of the sheet thickness reduction rate before and after the combining the elements is calculated as a difference between the sheet thickness reduction rates of these extracted elements. Also regarding the maximum principal strain, a difference is calculated between elements at closest positions from each other before and after the combining.

Then, an element having a difference of the sheet thickness reduction rate or the maximum principal strain larger than a predetermined value before and after the above-described combining of elements is extracted as a fracture risk portion (extracting unit (step) 25).

The method of obtaining the predetermined value is the same as in the extraction of FIG. 1 (extracting unit (step) 15).

The above-described analysis (analyzing unit (step) 22) and calculation (calculating unit (step) 24) may be executed successively in the same computer. Alternatively, after the analysis (analyzing unit (step) 22) is executed in one computer, the sheet thickness reduction rate or the maximum principal strain of each element as an analysis result thereof may be inputted to another computer (input unit (step) 23) so as to execute the calculation (calculating unit (step) 24) and the extraction (extracting unit (step) 25).

The present invention according to 6. is similar to the present invention according to 4., where the structure of the present invention according to 4. is applied to the present invention according to 5.

The present invention according to 7. is an invention of a processing device corresponding to the invention of the fracture prediction method according to 1., where the steps in FIG. 1 may be replaced by units.

As the analyzing unit 12, the same software as the commercially available software explained in the invention according to 1. may be installed and used.

This device has an input unit 13 inputting the sheet thickness reduction rate or the maximum principal strain obtained for each discretized element to another computer. As the input unit, a keyboard, a mouse, various types of digitizers or the like can be used.

Here, the input unit 13 and the extracting unit 15 may be in a separate device structure from the discretizing unit 11 and the analyzing unit 12. In this case, by inputting a result from formation analysis performed in one computer to another computer as original data, the processing can be performed in parallel, and thereby an effect of improved efficiency can be obtained.

The present invention according to 8. is an invention of a processing device corresponding to the invention of the fracture prediction method according to 2., where the steps in FIG. 1 may be replaced by units.

The invention according to 9. is an invention of a processing device corresponding to the invention of the fracture prediction method according to 5, where the steps in FIG. 5 may be replaced by units.

Here, the input unit 23, the calculating unit 24 and the extracting unit 25 may be in a separate device structure from the discretizing unit 21 and the analyzing unit 22. In this case, by inputting a result from forming analysis performed in one computer to another computer as original data, the processing can be performed in parallel, and thereby an effect of improved efficiency can be obtained.

The invention according to 10. is an invention of a computer program product corresponding to the fracture prediction method according to 1., which is a computer program product for implementing the respective steps in FIG. 1.

The input step 13 may be a step of inputting with a keyboard, or may be a step of inputting (reading data) the sheet thickness reduction rate or the maximum principal strain calculated in the analysis step 12 automatically to the extracting step 15 in the program product.

The present invention according to 11. is an invention of a computer program product corresponding to the fracture prediction method according to 2., and is a computer program product for implementing the respective steps in FIG. 1.

The present invention according to 12. is an invention of a computer program product corresponding to the fracture prediction method according to 3., and is a computer program product for implementing the respective steps in FIG. 1.

The present invention according to 13. is an invention of a computer program product corresponding to the fracture prediction method according to 4., and is a computer program product for implementing the respective steps in FIG. 1.

The present invention according to 14. is an invention of a computer program product corresponding to the fracture prediction method according to 5., and is a computer program product for implementing the respective steps in FIG. 5.

The input step 23 may be a step of inputting with a keyboard, or may be a step of inputting (reading data) the sheet thickness reduction rate or the maximum principal strain calculated in the analysis step 22 automatically to the extracting step 24 in the program product.

The present invention according to 15. is an invention of a computer program product corresponding to the fracture prediction method according to 6., and is a computer program product for implementing the respective steps in FIG. 5.

The invention according to 16. is a computer readable recording medium characterized by recording a computer program product according to any one of the above-described 10. to 15., namely, a flexible disk, a CD-ROM, or the like.

Example 1

Figure 6:
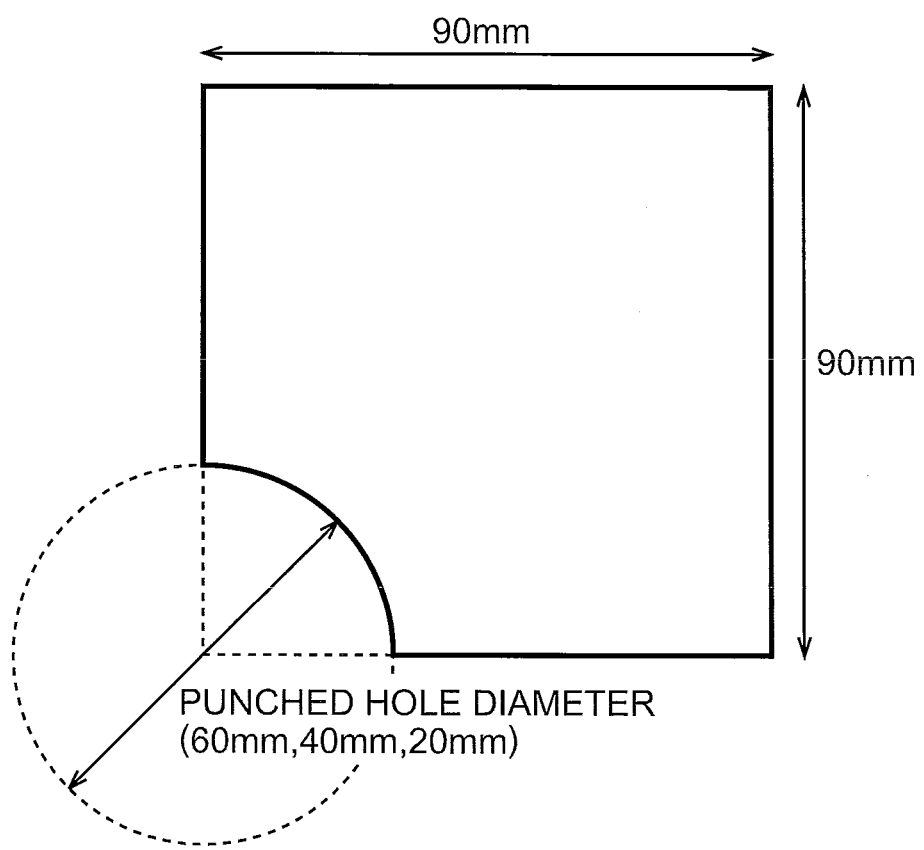
FIG. 6 is an explanatory view of a material sheet used for a forming experiment.
Figure 7A:
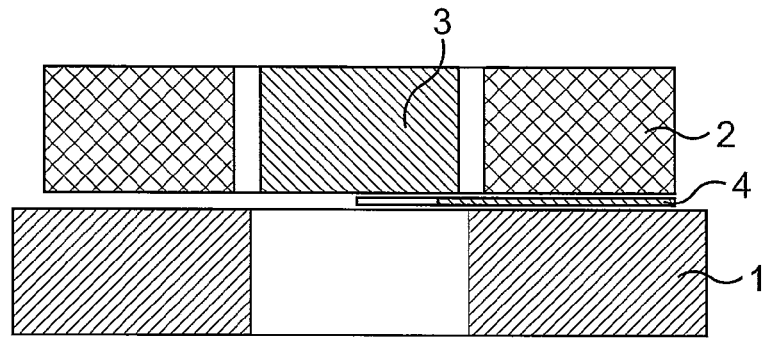
FIG. 7A is a schematic view showing a vertical cross-section before starting a flange-up forming test.
Figure 7B:
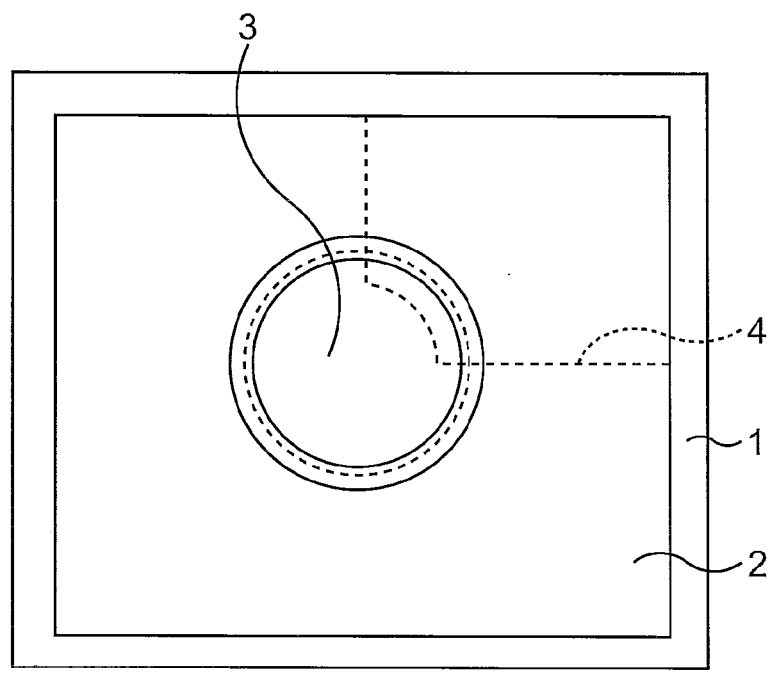
FIG. 7B is a schematic view showing a flat surface before starting the flange-up forming test.
Figure 7C:
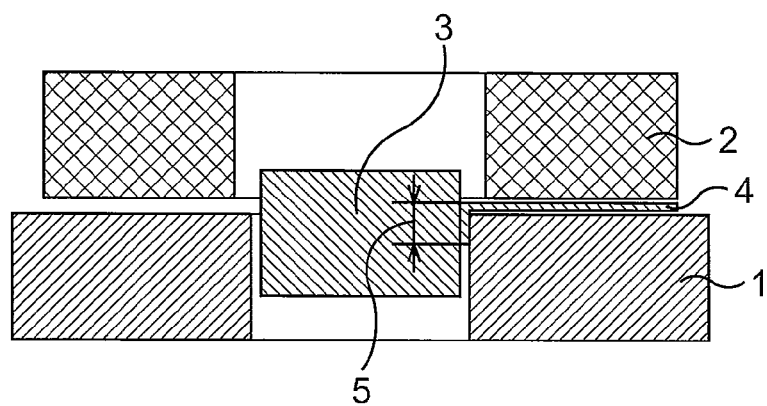
FIG. 7C is a schematic view showing a vertical cross-section after finishing the flange-up forming test.

The present invention will be explained below by way of presenting actual examples. A forming experiment was performed such that a material sheet shape of a hole expansion test by a cylindrical punch which is normally conducted is divided, and a flange-up forming is imitated. Specifically, a 180-mm square material sheet provided with a hole (diameter: 60 mm, or 40 mm, 20 mm) at the center was cut to ¼ as shown in FIG. 6, and as shown in FIG. 7A to FIG. 7C, a sheet to be processed 4 was held on a 106φ die 1 with a shoulder R of 5 mm by a blank holder 2, and thereafter the formation was performed using a 100φ cylindrical flat-bottom punch 3 with a shoulder R of 10 mm. At this time, the flange-up height 5 is about 20 mm for a hole diameter of 60 mm, about 30 mm for a hole diameter of 40 mm, and about 40 mm for a hole diameter of 20 mm. As the material, a cold-rolled steel of 440 MPa class having a sheet thickness of 1.6 mm was used. The forming was performed with a group of four sheets in the experiment. Consequently, as the summary is shown in Table 1, a fracture was generated in a center portion for the case of 60-mm hole diameter, but no fracture was generated and the flange-up forming was possible in the case of 40 mm and 20-mm hole diameters.

Finite element method analysis simulating this experimental result was performed. There were prepared material sheets discretized into elements by two types of area (each element discretized in a mesh form) sizes, about 2 mm (FIG. 8A) and about 4 mm (FIG. 8B). Using shape data created by CAD, the discretizing was performed automatically by a computer with the number of discretized elements of a circumferential portion being specified.

Other analysis conditions were the same for the both types. The formation analysis was performed with PAM-STAMP. The maximum principal strain after forming and the value of the sheet thickness were extracted for each discretized element from the entire analyzed data, and a sheet thickness reduction rate was calculated from the sheet thickness after formation as (initial sheet thickness−sheet thickness after forming)/(initial sheet thickness). The obtained value was outputted with the position information of each element in the circumferential portion and was inputted to a computer for data analysis.

Figure 9:
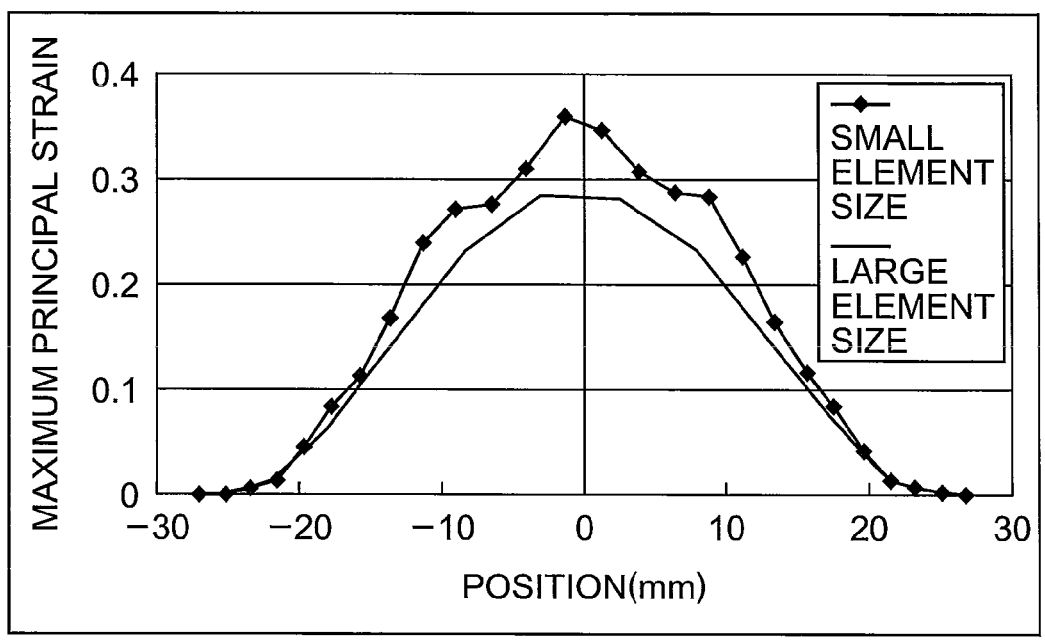
FIG. 9 is a characteristic chart showing analysis results of a maximum principal strain distribution with large and small elements.

FIG. 9 is a characteristic chart showing data of the maximum principal strain inputted to the computer for data analysis regarding the cases of the small element size (about 2 mm) and the large element size (about 4 mm) respectively. As shown here, it was found that, in the case of the small element size, the largest value of the maximum principal strain is large and the distribution is steep. This can be conceived to indicate that a large deformation gradient is generated at the center portion of the circumference under this condition. First, the position of an element to have the largest value of the maximum principal strain in the case of the small element size and the absolute value thereof were obtained. Thereafter, in the computer for data analysis, a position closest to the element that takes the largest value in the case of the small element size was found in calculation results of the large element size, and the absolute value of the maximum principal strain thereof was obtained. Finally, the difference between the two absolute values was calculated on the computer. Such an operation is equivalent to taking the difference between peak values of results of the large and small element sizes in FIG. 9.

Results thereof are shown in Table 1. Further, differences of sheet thickness reduction rate obtained similarly are also shown in the same table. While differences in the case of the 60-mm hole diameter are large, the differences become smaller as the hole diameters become smaller. A large difference indicates that a deformation gradient is larger, and corresponds to generation of a fracture with the 60-mm hole diameter in the experiment. In this example, a fracture portion is a stretch flange deformation and is in a state of uniaxial tension, and the sheet thickness reduction rate in the case of an isotropic material is about ½ of the maximum principal strain. Therefore, either one may be used as an analysis determination value, but it is desirable to use the maximum principal strain having a large absolute value so as to clarify the difference. In this example, the absolute value of a difference of an analysis value as the predetermined value for determination as a fracture risk portion is difficult to be found because it changes depending on the element size used, but in the range of consideration this time, it is conceivable that use of approximately 0.05 for the maximum principal strain and approximately 0.025 for the sheet thickness reduction rate will suffice.

Figure 8A:
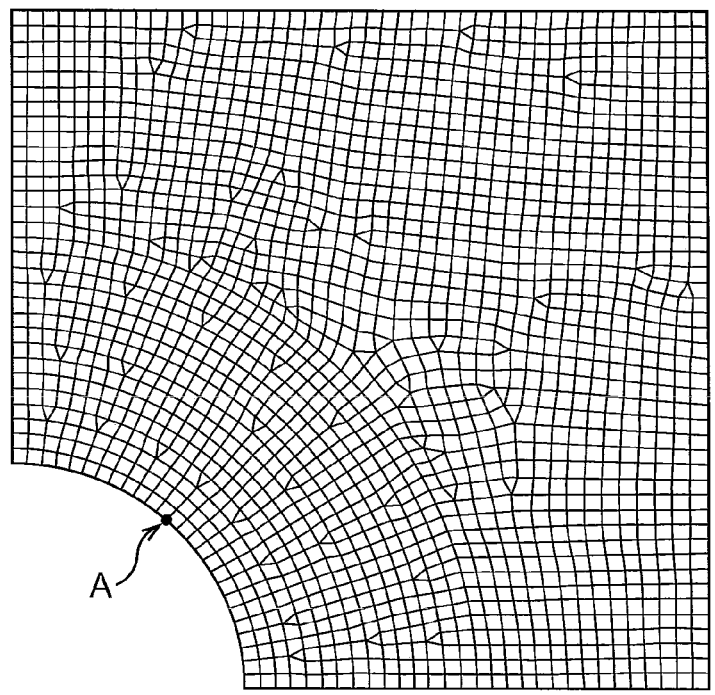
FIG. 8A is a schematic view showing element discretization by a small size used for forming analysis.
Figure 8B:
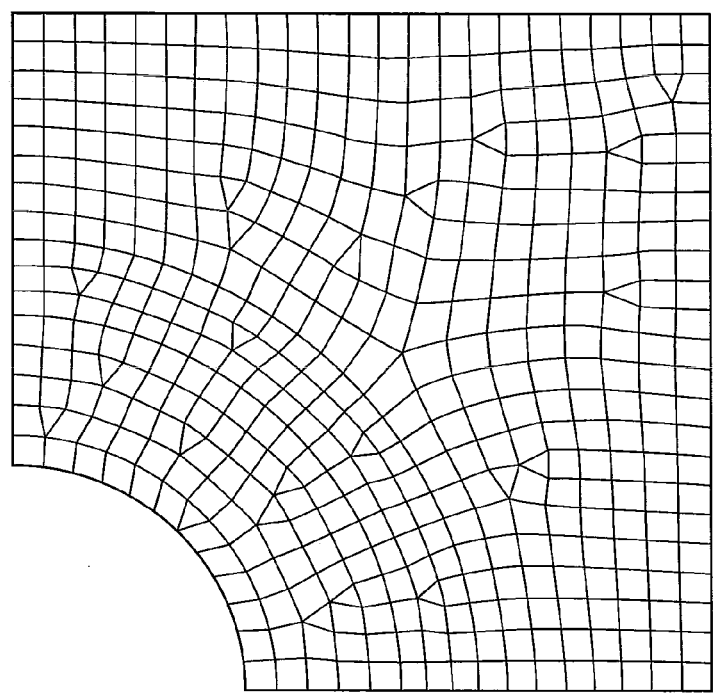
FIG. 8B is a schematic view showing element discretization by a large size used for forming analysis.

Here, the fracture prediction portion determined in this embodiment is shown by point A in FIG. 8A.

TABLE 1

| HOLE DIAMETER (mm) | RESULTS OF FORMIMG EXPERIMENT | DIFFERENCE OF ANALYSIS VALUE BETWEEN LARGE ELEMENT AND SMALL ELEMENT | | DETERMINATION BY ANALYSIS | CORRESPONDENCE BETWEEN EXPERIMENT AND ANALYSIS |
|---|---|---|---|---|---|
| | | MAXIMUM PRINCIPAL STRAIN | SHEET THICKNESS REDUCTION RATE | | |
| 60 | N.G.: CRACKED AT CENTER | 0.074 | 0.039 | N.G. | GOOD |
| 40 | O.K.: FORMING POSSIBLE | 0.029 | 0.017 | O.K. | GOOD |
| 20 | O.K.: FORMING POSSIBLE | 0.012 | 0.017 | O.K. | GOOD |

Example 2

Two or more adjacent elements were combined using the analysis results with the 60-mm hole diameter and the small element size (about 2 mm) in Example 1, a deformation gradient was evaluated by comparing the difference before and after combining. Thus, whether fracture determination is possible or not was examined.

Element discretization and formation analysis were performed similarly to the case of the small element size in Example 1 (FIG. 8A).

Analysis values of the elements (particularly around the vicinity of elements in which analysis values peak) were output in advance from formation analysis results together with position information thereof. The data thereof were inputted to the computer for data analysis, the arithmetic average of analysis values were calculated for each of 2 to 5 combined adjacent elements selected this time, and the difference with the maximum value of analysis values of the initial analysis was calculated.

The difference between the maximum value obtained from a distribution of maximum principal strains when the two adjacent elements were averaged and the maximum value before averaging was 0.007, the difference from the average value of three elements was 0.02, the difference from the average value of four elements was 0.035, and the difference from the average value of five elements was 0.040. The values were small compared to those calculated with the element size being actually changed as shown in Example 1, but it was found that extracting the size of a deformation gradient, namely a fracture risk portion, is possible by taking the difference between an analysis value calculated with an element combined from plural adjacent elements and an analysis value before combining. At this time, about how many elements should be combined is determined by a ratio of the size of the deformation gradient to the size of the element after combining, but it is preferable to take plural numbers of elements to be combined and check dependency of the difference of the analysis values. In this example, it was found that, when differences between the average value from combining four elements and analysis values before the combining are taken, fracture determination is possible by setting approximately 0.03 or larger of the maximum principal strain as a predetermined value at which a fracture occurs.

Example 3

It was examined whether fracture prediction of materials having various strength is possible or not under the test condition of the 40-mm hole diameter in Example 1. The materials used range from mild steel to a steel sheet of 980 MPa class shown in Table 2. Ones having a sheet thickness of 1.6 mm were used.

As a result of conducting an experiment, a stretch flange crack occurred in the center of a portion to be flanged up in the 980 MPa class steel sheet. Finite element method analysis was performed under the same conditions as the experiment. The analysis was performed with two types of element sizes, about 2 mm and about 4 mm. As shown in FIG. 8A and FIG. 8B, edge portions are connected smoothly without any recess or projection, and to be careful about making the element size change surely along the edge portions, discretizing of edge portions was automatically performed by a computer with the number of discretizations on the circumferential part being specified. Forming analysis and calculation of the maximum principal strain and the sheet thickness reduction rate in each element were performed similarly to Example 1.

The difference of maximum values of the maximum principal strain and the sheet thickness reduction rate after the flange-up forming under the respective conditions were calculated, with forming analysis results being outputted, by the computer for data analysis similarly to Example 1. Results thereof are shown in Table 2. It can be seen that the differences become larger as the material strength become higher, and the deformation gradients at deformation concentrated portion are large. Similarly to Example 1, when a difference of 0.05 or larger of the maximum principal strain is determined to be a fracture, it was found that a fracture was determined with the 980 MPa class steel sheet, and this coincides with the experimental results.

TABLE 2

| | MATERIAL | | | | | DIFFERENCE OF ANALYSIS VALUE BETWEEN LARGE ELEMENT AND SMALL ELEMENT | | PLATE | CORRESPONDENCE |
|---|---|---|---|---|---|---|---|---|
| STEEL TYPE | YIELD STRENGTH (MPa) | EXTENSION STRENGTH (MPa) | STRETCH (%) | RESULTS OF FORMATION EXPERIMENT | MAXIMUM PRINCIPAL STRAIN | THICKNESS REDUCTION RATE | DETERMINATION BY ANALYSIS | BETWEEN EXPERIMENT AND ANALYSIS |
| SOFT STEEL | 190 | 326 | 43 | O.K.: FORMATION POSSIBLE | 0.018 | 0.008 | O.K. | GOOD |
| 440 MPa CLASS | 295 | 449 | 36 | O.K.: FORMATION POSSIBLE | 0.029 | 0.017 | O.K. | GOOD |
| 590 MPa CLASS | 340 | 612 | 33 | O.K.: FORMATION POSSIBLE | 0.035 | 0.021 | O.K. | GOOD |
| 980 MPa CLASS | 752 | 1034 | 15 | N.G.: CRACKED AT CENTER | 0.068 | 0.031 | N.G. | GOOD |

Other Embodiments of Applying the Present Invention

The fracture prediction method in the above-described embodiment (discretizing step 11 to extracting step 15 of FIG. 1, discretizing step 21 to extracting step 25 of FIG. 25, and so on) can be realized by operation of a program product stored in a RAM, ROM, or the like of a computer. This program product and a computer readable recording medium recording this program product are included in the present invention.

Specifically, the program product is provided to a computer by being recorded in a recording medium such as CD-ROM or via various types of transmission media for example. As the recording medium recording the program product, a flexible disk, a hard disk, a magnetic tape, a magneto-optical disk, a non-volatile memory card, or the like can be used other than the CD-ROM. On the other hand, as the transmission medium of the program product, it is possible to use a communication medium in a computer network system for propagating program information as carrier waves for supplying. Here, the computer network is a LAN, a WAN such as the Internet, a radio communication network, or the like, and the communication medium is a wired line of optical fiber or the like, a wireless line, or the like.

Further, the program product included in the present invention is not only such a type that the functions of the above-described embodiment are realized by a computer executing a supplied program product. For example, when the program product cooperates with the OS (operating system) operating on a computer, another application software, or the like to realize the functions of the above-described embodiment, such a program product is included in the present invention. Further, when all or part of processing of the supplied program product is performed by a function expansion board or a function expansion unit of a computer to realize the functions of the above-described embodiment, such a program product is included in the present invention.

Figure 10:
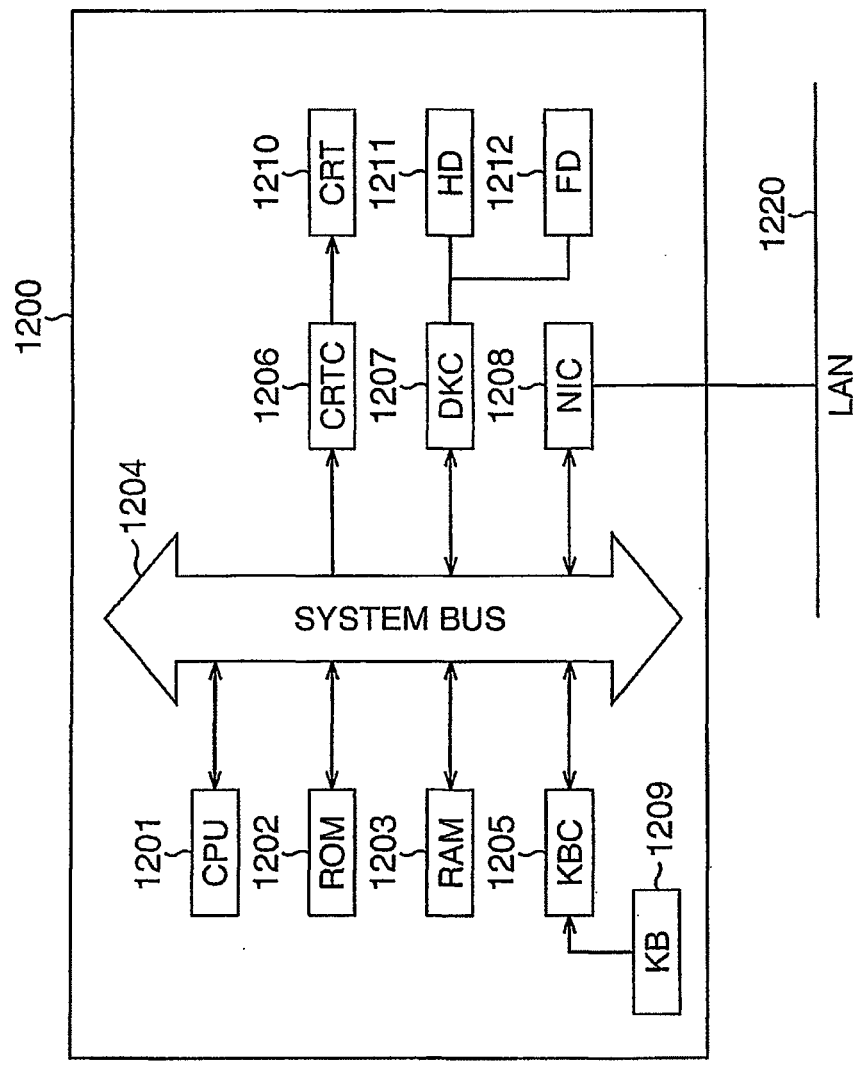
FIG. 10 is a schematic diagram showing an internal structure of a personal user terminal device.

For example, FIG. 10 is a schematic diagram showing an internal structure of a personal user terminal device. In this FIG. 10, 1200 denotes a personal computer including a CPU 1201. The PC 1200 executes device control software stored in a ROM 1202 or a hard disk (HD) 1211 or supplied by a flexible disk drive (FD) 1212. This PC 1200 controls overall operations of devices coupled to a system bus 1204.

By the program stored in the CPU 1201, the ROM 1202 or the hard disk (HD) 1211 of the PC 1200, procedures of discretizing step 11 to extracting step 15 of FIG. 1, and discretizing step 21 to extracting step 25 of FIG. 5, or the like of this embodiment are realized.

1203 denotes a RAM, and functions as the main memory, a work area, or the like for the CPU 1201. 1205 denotes a keyboard controller (KBC), and controls instruction inputs from a keyboard (KB) 1209, a not-shown device, or the like.

1206 denotes a CRT controller (CRTC), and controls display on a CRT display (CRT) 1210. 1207 denotes a disk controller (DKC). The DKC 1207 controls access to the hard disk (HD) 1211 storing a boot program, plural applications, an edit file, a user file, as well as a network administration program, and so on, and to the flexible disk (FD) 1212. Here, the boot program refers to a startup program, a program that starts execution (operation) of hardware and/or software of a personal computer.

1208 denotes a network interface card (NIC), and performs bidirectional exchange of data with a network printer, another network device, or another PC via the LAN 1220.

INDUSTRIAL APPLICABILITY

By performing fracture prediction of a part to be processed based on the present invention, dependency on selection of analysis conditions can be reduced, and a fracture risk portion can be extracted easily and reliably. Accordingly, the costs needed for development can be reduced, and weight reduction is realized by applying a material having higher strength to a part to be processed.

What is claimed is:
1. A fracture prediction method comprising:
   discretizing an analysis target area by a first area and a second area larger than the first area, respectively, and performing forming analysis using a finite element method;
   calculating, in a computer, maximum principal strain or sheet thickness reduction rate values for each of the first area and the second area; and extracting a position of a fracture risk area of the analysis target area discretized by the first area, where a difference of maximum principal strain or sheet thickness reduction rate values between the calculated values at the position in the first area and those at a corresponding position in the second area is larger than a predetermined value.

2. The fracture prediction method according to claim 1, wherein in said discretizing the analysis target area, a size of the first area and a size of the second area are determined by a relationship with a work hardening property n of the analysis target area.

3. The fracture prediction method according to claim 1, wherein in said extracting the position of the fracture risk area, when the difference larger than the predetermined value is not extracted, at least the first area out of the first area and the second area is set smaller, and the discretizing, calculating, and extracting steps are executed again sequentially.

4. The fracture prediction method according to claim 1, wherein in said discretizing the analysis target area, an edge portion of the analysis target area is discretized, and then the forming analysis is performed.

5. A fracture prediction method comprising:
discretizing an analysis target area into plural areas, and performing forming analysis using a finite element method;
calculating, in a computer, maximum principal strain or sheet thickness reduction rate values for each of the areas;
combining adjacent two or more of the areas and a calculating maximum principal strain value or a sheet thickness reduction rate value in the combined area; and
extracting a position of a fracture risk area of the analysis target area, where a difference of the maximum principal strain or the sheet thickness reduction rate values before and after combining the areas is larger than a predetermined value.

6. The fracture prediction method according to claim 5, wherein in said discretizing of the analysis target area, an edge portion of the analysis target area is discretized, and then the forming analysis is performed.

7. A processing device configured to perform a fracture prediction method of an analysis target area, the processing device comprising:
a discretizing unit configured, in a computer, to discretize an analysis target area by a first area and a second area larger than the first area respectively and performing forming analysis using a finite element method;
a calculating unit configured, in the computer, to calculate a maximum principal strain value or a sheet thickness reduction rate value for the area discretized by the first area and the second area; and
an extraction unit configured, in the computer, to extract a position of a fracture risk area from the analysis target area discretized by the first area, where a difference of maximum principal strain or sheet thickness reduction rate between the calculated values at the position in the first area and those at a corresponding position in the second area is larger than a predetermined value.

8. The processing device according to claim 7, wherein the discretizing unit determines a size of the first area and a size of the second area by a relationship with a work hardening property n of the analysis target area.

9. A processing device configured to perform a fracture prediction method of an analysis target area, the processing device comprising:
a discretizing unit configured, in a computer, to discretize an analysis target area into plural areas, and performing forming analysis using a finite element method;
a calculating unit configured, in the computer, to calculate maximum principal strain value or a sheet thickness reduction rate value for each of the areas;
a combining unit configured, in the computer, to combine adjacent two or more areas and to calculate the maximum principal strain value or sheet thickness reduction rate value in the combined area; and
an extraction unit configured, in a computer, to extract a position of a fracture risk area of the analysis target area, where a difference of the maximum principal strain or the sheet thickness reduction rate values before and after combining the areas is larger than a predetermined value.

10. A non-transitory computer readable recording medium recording a program product which when executed by a computer causes the computer to perform a method comprising:
discretizing an analysis target area by a first area and a second area larger than the first area respectively and performing forming analysis using a finite element method;
calculating, in a computer, maximum principal strain or sheet thickness reduction rate values for the area discretized by the first area and the second area; and
extracting a position of a fracture risk area of the analysis target area discretized by the first area, where difference of maximum principal strain or sheet thickness reduction rate values between the calculated values at the position in the first area and those at a corresponding position in the second area is larger than a predetermined value.

11. The non-transitory computer readable recording medium according to claim 10, wherein in said discretizing the analysis target area, a size of the first area and a size of the second area are determined by a relationship with a work hardening property n of the analysis target area.

12. The non-transitory computer readable recording medium according to claim 10, wherein in said extracting the position of the fracture risk area, when the difference larger than the predetermined value is not extracted, at least the first area out of the first area and the second area is set smaller, and the discretizing, calculating, and extracting steps are executed again sequentially.

13. The non-transitory computer readable recording medium according to claim 10, wherein in said discretizing the analysis target area, an edge portion of the analysis target area is discretized, and then the forming analysis is performed.

14. A non-transitory computer readable recording medium recording a program product which when executed by a computer causes the computer to perform:
discretizing an analysis target area into plural areas, and performing forming analysis using a finite element method;
calculating, in a computer, maximum principal strain or sheet thickness reduction rate values for each of the areas;
combining adjacent two or more of the areas and calculating a maximum principal strain value or sheet thickness reduction rate value in the combined area; and
extracting a position of a fracture risk area of the analysis target area, where a difference of the maximum principal strain or the sheet thickness reduction rate values before and after combining the areas is larger than a predetermined value.

15. The non-transitory computer readable recording medium according to claim 14,
wherein in said discretizing of the analysis target area, an edge portion of the analysis target area is discretized, and then the forming analysis is performed.

\* \* \* \* \*